United States Patent
Chak et al.

(10) Patent No.: US 12,376,875 B2
(45) Date of Patent: Aug. 5, 2025

(54) ENDOSCOPIC TISSUE RESECTION DEVICE

(71) Applicant: UNIVERSITY HOSPITALS CLEVELAND MEDICAL CENTER, Cleveland, OH (US)

(72) Inventors: Amitabh Chak, University Heights, OH (US); Jeffrey Marks, Solon, OH (US); Steve Schomisch, Strongsville, OH (US); Ryan Juza, Broadview Heights, OH (US)

(73) Assignee: UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 229 days.

(21) Appl. No.: 18/261,050

(22) PCT Filed: Jan. 20, 2022

(86) PCT No.: PCT/US2022/070261
§ 371 (c)(1),
(2) Date: Jul. 11, 2023

(87) PCT Pub. No.: WO2022/159956
PCT Pub. Date: Jul. 28, 2022

(65) Prior Publication Data
US 2024/0090912 A1    Mar. 21, 2024

Related U.S. Application Data

(60) Provisional application No. 63/140,013, filed on Jan. 21, 2021.

(51) Int. Cl.
*A61B 17/3205* (2006.01)
*A61B 1/00* (2006.01)
(Continued)

(52) U.S. Cl.
CPC .......... *A61B 17/320016* (2013.01); *A61B 2017/00296* (2013.01); *A61B 2017/00358* (2013.01); *A61B 2017/306* (2013.01)

(58) Field of Classification Search
CPC ...... A61B 17/320016; A61B 17/32056; A61B 2017/00296; A61B 2017/00358;
(Continued)

(56) References Cited

U.S. PATENT DOCUMENTS

| | | |
|---|---|---|
| 10,786,256 B2 | 9/2020 | Smith et al. |
| 10,791,911 B2 | 10/2020 | Wales et al. |

(Continued)

FOREIGN PATENT DOCUMENTS

| | | |
|---|---|---|
| WO | 2018065899 A1 | 4/2018 |
| WO | 2020191132 A1 | 9/2020 |

OTHER PUBLICATIONS

Search Report and Written Opinion for International Application No. PCT/US2022/070261 mailed Mar. 25, 2022, pp. 1-6.

*Primary Examiner* — Anh T Dang
(74) *Attorney, Agent, or Firm* — EVENTIDE LAW LLC

(57) ABSTRACT

An endoscopic tissue resection device configured to be attached at a distal tip of an endoscope is disclosed. The device comprises a cap, a snare sheath, a snare, and a spring wire. The snare comprises a collapsible snare wire configured to be retracted from the cavity of the cap into the snare sheath, the collapsible snare wire reversibly collapsing upon retraction, and to be advanced from the snare sheath into the cavity of the cap, the collapsible snare wire reversibly expanding upon advancement. The spring wire is reversibly deflectable from a resting state to a deflected state. In the resting state the spring wire orients and stabilizes an apex of the collapsible snare wire within the cap such that two (Continued)

opposing wire portions of the collapsible snare wire are positioned in apposition to a distal opening of the cap.

13 Claims, 12 Drawing Sheets

(51) Int. Cl.
*A61B 17/32* (2006.01)
*A61B 17/00* (2006.01)
*A61B 17/30* (2006.01)

(58) Field of Classification Search
CPC .... A61B 2017/306; A61B 2017/00269; A61B 2017/308; A61B 1/0089; A61B 1/00133; A61B 1/00089; A61B 2018/00494; A61B 2018/00601; A61B 2018/00982; A61B 18/082

See application file for complete search history.

(56) References Cited

U.S. PATENT DOCUMENTS

| | | |
|---|---|---|
| 10,799,262 B2 | 10/2020 | Chae |
| 10,835,270 B2 | 11/2020 | Saunders et al. |
| 2004/0158127 A1* | 8/2004 | Okada .................. A61B 18/14 600/104 |
| 2014/0378989 A1 | 12/2014 | Raybin et al. |
| 2018/0000321 A1 | 1/2018 | Wales et al. |
| 2018/0140320 A1* | 5/2018 | Aikawa .............. A61B 18/1492 |

* cited by examiner

ENDOSCOPIC TISSUE RESECTION DEVICE

REFERENCE TO RELATED APPLICATIONS

This application claims the benefit of U.S. Provisional Application No. 63/140,013, filed on Jan. 21, 2021, which is hereby incorporated by reference.

FIELD OF THE INVENTION

The present invention relates generally to devices for intraluminal endoscopic tissue resection, and more particularly to devices for intraluminal endoscopic tissue resection including a cap, a snare sheath, a snare, and a spring wire.

BACKGROUND OF THE INVENTION

Endoscopic intraluminal tissue resection is a challenging procedure.

Endoscopic snares are commonly used to biopsy and remove polyps or tissue during colonoscopy and upper endoscopy to evaluate for cancer. Commercially available endoscopic snares are used through the working channel of the endoscope. The snare is a wire loop retracted into an outer sheath. When deployed, the snare forms a loop and is positioned around the tissue of concern and then closed to snare, capture, and incise the encircled tissue. If the specimen is small enough, the specimen can then be removed through the same working channel of the endoscope with suction. Larger specimens are captured in an endoscopic net and removed with the endoscope.

The snare wire must be flexible for it to be retracted into the sheath to grasp the tissue. Paradoxically, the more flexible the snare, the more difficult it is to engage tissue. The snare frequently slips off the tissue.

Therefore, precise, efficient, repeatable tissue resection is challenging or impossible in some anatomical locations. Because the snare sheath occupies the only channel within the endoscope, a secondary device to aid in tissue resection cannot be used. An endoscopic distal attachment, also termed a "distal cap attachment" or a "cap," can be combined with a snare. The cap allows the use of suction to retract the tissue. However, positioning the snare within the cap is still a technical challenge.

There is a need for a device capable of efficient, precise, repeatable endoscopic tissue resection.

SUMMARY OF THE INVENTION

An endoscopic tissue resection device configured to be attached at a distal tip of an endoscope is disclosed. The device comprises a cap, a snare sheath, a snare, and a spring wire.

The cap comprises a cap body, a proximal end, a proximal opening, a distal end, and a distal opening. The cap body defines a cavity for retraction of a tissue and has an inner perimeter.

The snare sheath comprises a proximal end, a distal end, and a snare sheath body therebetween. The distal end of the snare sheath is affixed to the cap body along the inner perimeter of the cap body.

The snare comprises a snare actuation cable and a collapsible snare wire.

The snare actuation cable comprises a proximal end, a distal end and a snare actuation cable body therebetween, is disposed within the snare sheath, and is configured to be translated proximally and distally within the snare sheath.

The collapsible snare wire comprises a base, an apex opposite the base, and two opposing wire portions extending therebetween, is disposed within the cavity of the cap, and is reversibly collapsible from an expanded state to a collapsed state. The base of the collapsible snare wire is attached to the snare actuation cable at or near the distal end of the snare actuation cable.

The collapsible snare wire is configured to be retracted from the cavity of the cap into the snare sheath by translating the snare actuation cable proximally within the snare sheath, the collapsible snare wire reversibly collapsing from the expanded state to the collapsed state upon retraction, and to be advanced from the snare sheath into the cavity of the cap by translating the snare actuation cable distally within the snare sheath, the collapsible snare wire reversibly expanding to the expanded state upon advancement.

The spring wire is disposed within the cavity of the cap and comprises a proximal end, a distal end, and a flexible portion therebetween. The proximal end of the spring wire is attached to the cap body at or near the proximal end of the cap. The distal end of the spring wire is attached to the apex of the collapsible snare wire.

The spring wire is reversibly deflectable from a resting state to a deflected state, the spring wire being in the resting state when the collapsible snare wire is disposed within the cavity of the cap and deflecting to the deflected state when the collapsible snare wire is retracted into the snare sheath. In the resting state the spring wire orients and stabilizes the apex of the collapsible snare wire within the cap, at or near the distal opening of the cap, opposite the distal end of the snare sheath, such that the two opposing wire portions of the collapsible snare wire are positioned in apposition to the distal opening of the cap. During deflection the spring wire bends along an arced path to the snare sheath.

The distal end of the snare sheath is recessed into the cavity of the cap relative to the distal end of the spring wire to allow the spring wire to bend along the arced path.

In some embodiments, the cap has an outer diameter of 0.5 to 1.5 cm.

In some embodiments, the cavity of the cap has an inner depth of 0.5 cm to 1.5 cm.

In some embodiments, the cavity of the cap has an inner diameter, the spring wire has a length, and the inner diameter of the cavity of the cap is greater than the length of the spring wire.

In some embodiments, the distal end of the cap has an oblique profile.

In some embodiments, the distal end of the cap comprises a lip within the cavity of the cap for retaining the collapsible snare wire within the cavity of the cap.

In some embodiments, the two opposing wire portions of the collapsible snare wire have an approximately hexagonal, circular, or elliptical shape in the expanded state.

In some embodiments, the distal opening of the cap has an inner circumference having a diameter, and the collapsible snare wire in the expanded state apposes the inner circumference of the distal opening of the cap closely enough that any gaps between the two opposing wire portions of the collapsible snare wire and the inner circumference of the distal opening of the cap are not more than 10%, 8%, 6%, 4%, or 2% of the diameter of the inner circumference of the distal opening of the cap.

In some embodiments, the distal opening of the cap has an inner circumference, and the collapsible snare wire in the expanded state apposes the inner circumference of the distal opening of the cap closely enough that any gaps between the two opposing wire portions of the collapsible snare wire and the inner circumference of the distal opening of the cap are not more than 5 mm, 4 mm, 3 mm, 2 mm, or 1 mm.

In some embodiments, the distal end of the cap has a distal edge, the cavity of the cap has an inner depth, and the collapsible snare wire in the expanded state rests sufficiently flush to the distal edge of the distal end of the cap that any gaps between the two opposing wire portions of the collapsible snare wire and the distal edge of the distal end of the cap are not more than 20%, 16%, 12%, 8%, or 4% of the inner depth of the cavity of the cap.

In some embodiments, the distal end of the cap has a distal edge, the cap has an axis extending from the proximal end of the cap to the distal end of the cap, and the collapsible snare wire in the expanded state rests sufficiently flush to the distal edge of the distal end of the cap that any gaps between the two opposing wire portions of the collapsible snare wire and the distal edge of the distal end of the cap are not more than 5 mm, 4 mm, 3 mm, 2 mm, or 1 mm as measured along the axis.

In some embodiments, the snare sheath has an axis extending from its proximal end to its distal end, and the collapsible snare wire is shaped to deflect from the axis during advancement of the collapsible snare wire from the distal end of the snare sheath.

In some embodiments, the device further comprises a blade disposed in the cavity of the cap adjacent the distal end of the snare sheath.

BRIEF DESCRIPTION OF THE DRAWINGS

These and other features, aspects, and advantages of the present disclosure are better understood when the following detailed description is read with reference to the accompanying drawings.

DETAILED DESCRIPTION OF THE INVENTION

Figure 1:
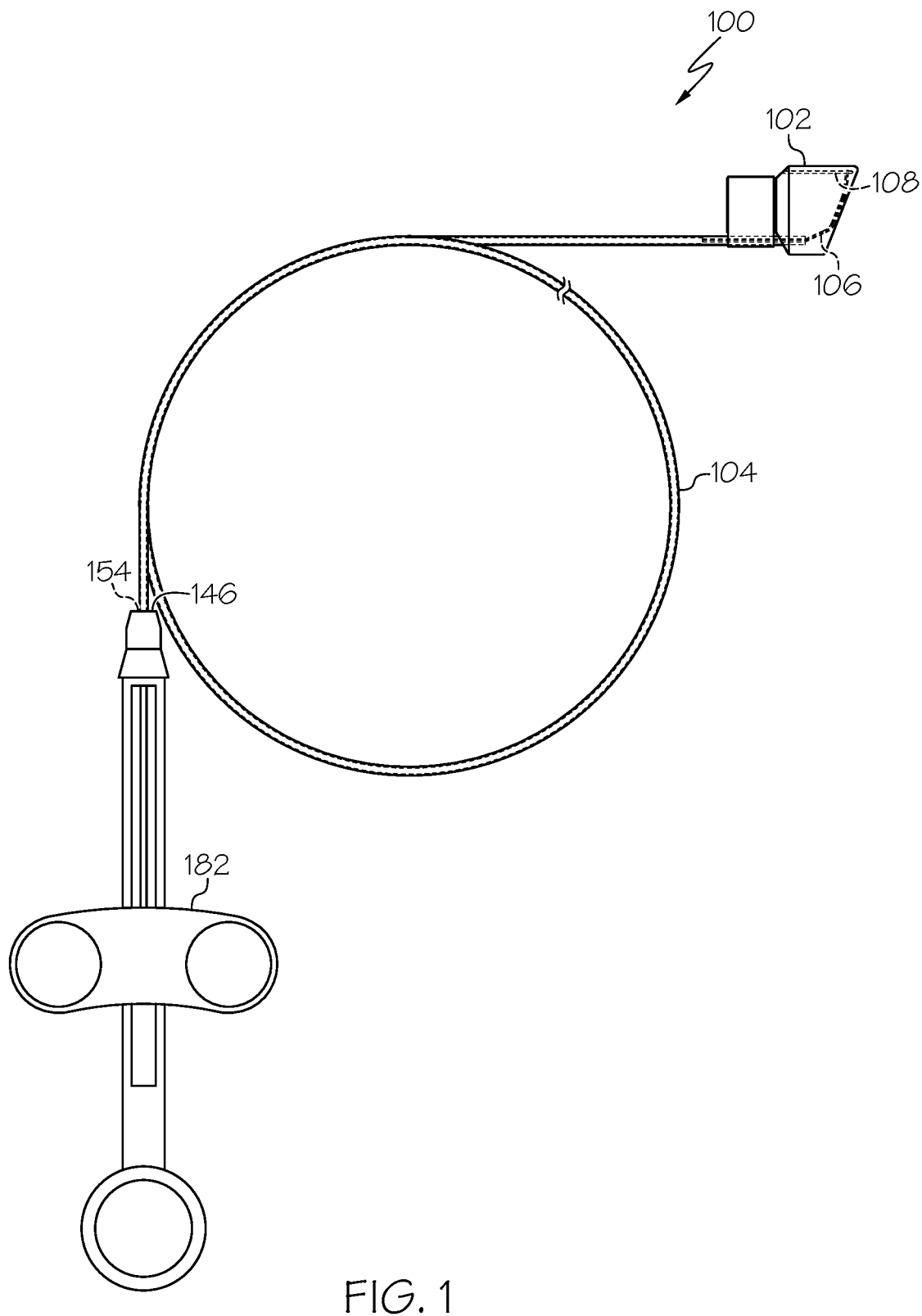
FIG. 1 is a top view of an embodiment of the endoscopic tissue resection device comprising a cap, a snare sheath, a snare, and a spring wire, the snare sheath and a portion of the snare being in a coiled configuration, and a snare actuator handle attached to the device. As shown, the device terminates proximally with the snare actuator handle and terminates distally at the cap.

An endoscopic tissue resection device 100 configured to be attached at a distal tip of an endoscope is disclosed (FIG. 1). The endoscopic tissue resection device 100 comprises a cap 102, a snare sheath 104, a snare 106, and a spring wire 108 that are configured in a manner that advantageously provides for more reliable, reproducible, and efficient tissue resection (FIGS. 1-16).

Figure 2:
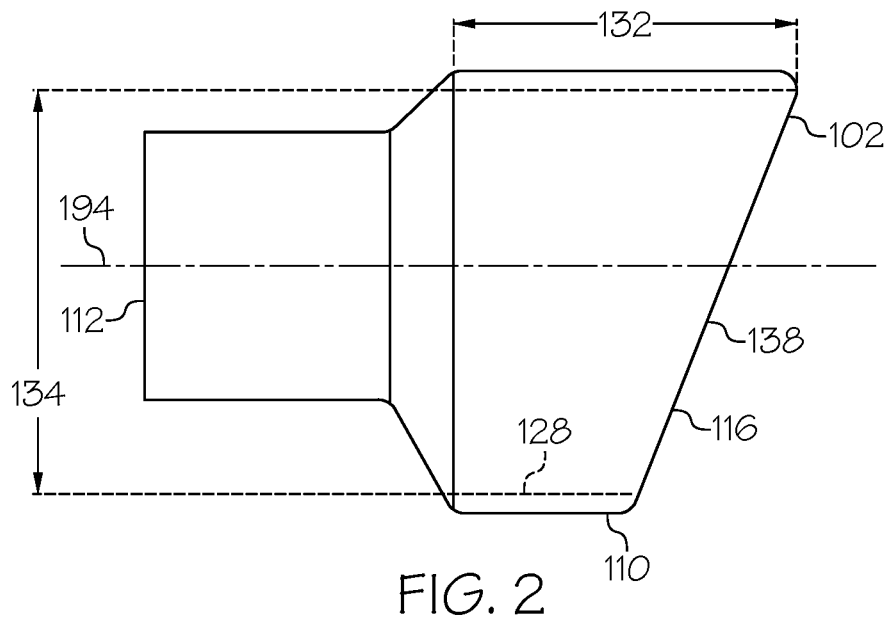
FIG. 2 is a side view of the cap of the endoscopic tissue resection device of FIG. 1.
Figure 3:
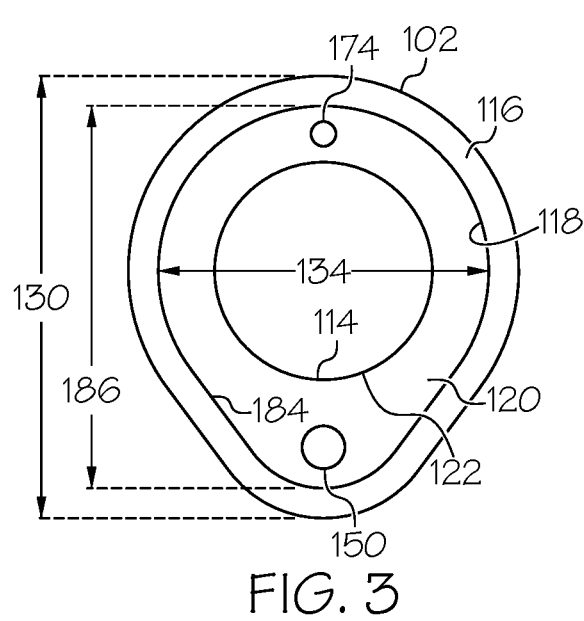
FIG. 3 is a front view of the cap of the endoscopic tissue resection device of FIG. 1.
Figure 4:
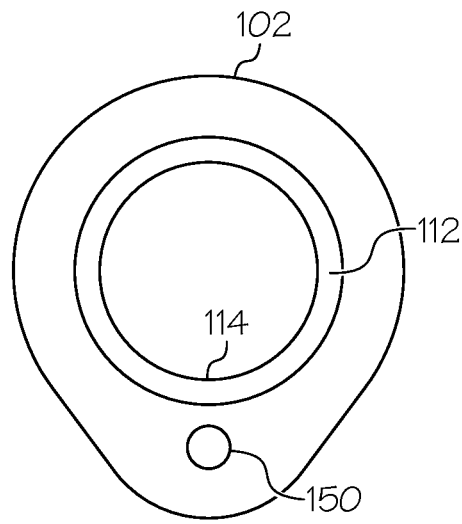
FIG. 4 is a back view of the cap of the endoscopic tissue resection device of FIG. 1.

The cap 102 comprises a cap body 110, a proximal end 112, a proximal opening 114, a distal end 116, and a distal opening 118 (FIGS. 2-4). The cap body 110 defines a cavity 120 for retraction of a tissue and has an inner perimeter 122.

The cap 102 can be made from a clear or translucent plastic or polymeric material to provide endoscopic visualization with minimal interference by the cap 102. The cap 102 can be made with smooth surfaces so as not to cause harm to a patient.

The cap 102 is dimensioned so that cap 102 can be attached to a distal tip of an endoscope, tissue can be retracted into the cavity 120 of the cap 102, and the spring wire 108 can flex along an arced path 124 within the cavity 120 of the cap 102 to a distal end 126 of the snare sheath 104. Regarding attachment of the cap 102 to the distal tip of an endoscope and retraction of tissue into the cavity 102 of the cap 102, the cap 102 can be provided with a range of outer diameters and inner depths. For example, the diameter of the cap 102 can range from approximately 0.5-1.5 cm and the depth of cap 102 can vary from approximately 0.5-1.5 cm. The cap 102 can also have a variable, e.g. adjustable, depth option, allowing for depth of tissue retracted. Regarding the spring wire 108 flexing along an arced path 124 within the cavity 120 of the cap 102, the cap 102 must have an inner diameter that is large enough to accommodate flexing of the spring wire 108 along the arced path 124 to the distal end 126 of the snare sheath 104. This is so that an inner surface 128 of the cap 102 does not impede flexing of the spring wire 108 along the arced path 124. This can be accomplished by providing the cap 102 with a cavity 120 having an inner diameter greater than the length of the spring wire 108. Thus, in some embodiments, the cap 102 has an outer diameter 130 of 0.5 to 1.5 cm. In some embodiments, the cavity 120 of the cap 102 has an inner depth 132 of 0.5 cm to 1.5 cm. In some embodiments, the cap 102 has a variable depth option. In some embodiments, the cavity 102 of the cap 102 has an inner diameter 134, the spring wire 108 has a length 136, and the inner diameter 134 of the cavity 120 of the cap 102 is greater than the length 136 of the spring wire 108.

Figure 11:
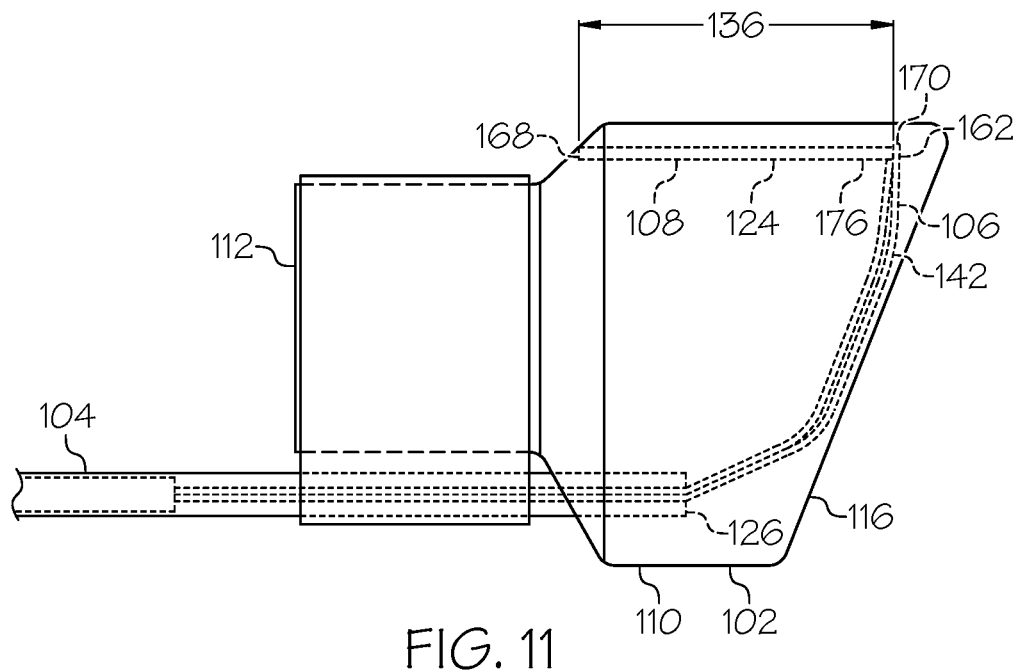
FIG. 11 is a side view of the cap, distal portions of the snare sheath and snare, and the spring wire as shown in FIG. 8.
Figure 12:
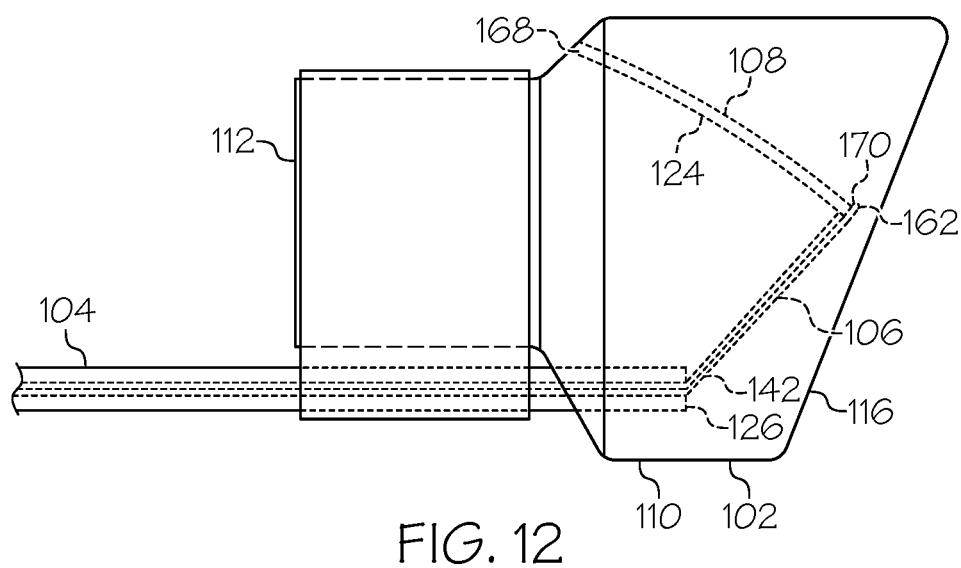
FIG. 12 is a side view of the cap, distal portions of the snare sheath and snare, and the spring wire as shown in FIG. 9.
Figure 13:
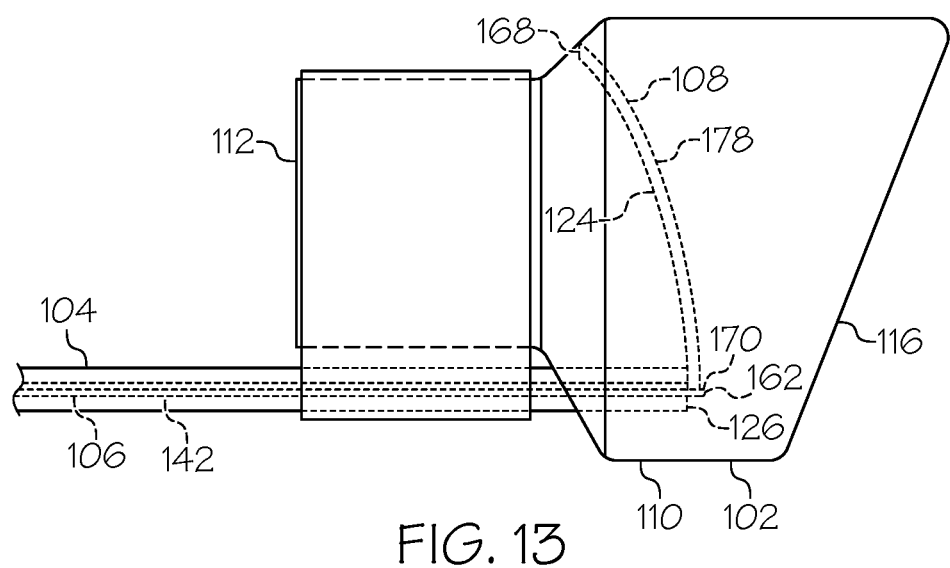
FIG. 13 is a side view of the cap, distal portions of the snare sheath and snare, and the spring wire as shown in FIG. 10.

The cap 102 is shaped to accommodate the arced path 124 of the spring wire 108 (FIGS. 11-13). For example, a cap 102 having an oblique profile at the distal end 116 of the cap 102 can be advantageous to better accommodate the arced path 124 of the spring wire 108 in comparison, for example, to a perpendicular profile. Thus, in some embodiments the distal end 116 of the cap 102 has an oblique profile 138.

In some embodiments, the orientation and/or shape of the cap 102 can be varied. For example, the orientation and/or shape of the cap 102 can be flat or beveled, circular or elliptical.

Figure 14:
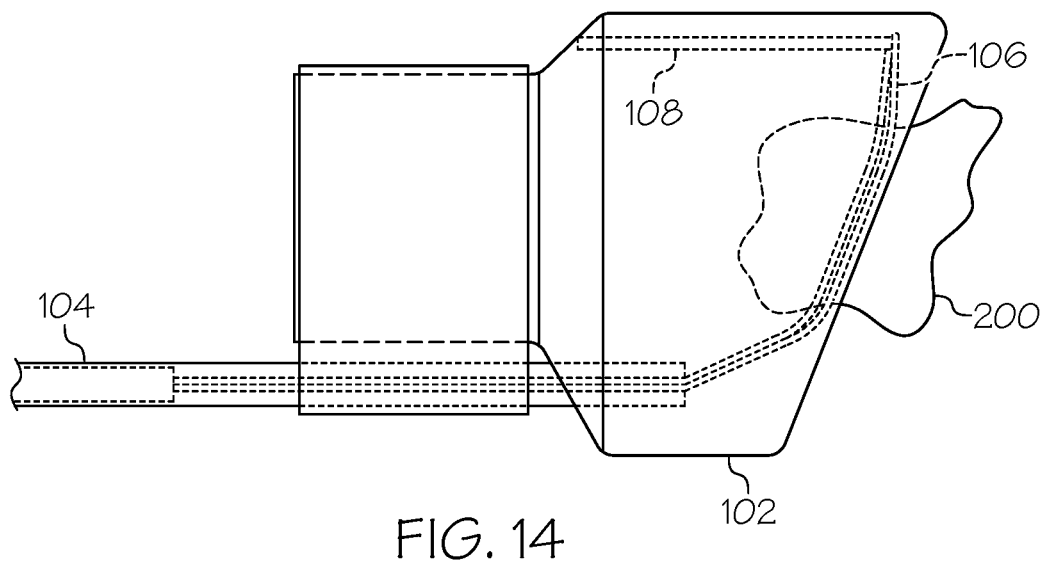
FIG. 14 is a side view of the cap, distal portions of the snare sheath and snare, and the spring wire as shown in FIG. 8, in which tissue has been retracted into the cap and is encircled by the collapsible snare wire of the snare.

In some embodiments, the cap 102 can comprise a lip 140 at the distal end 116 of the cap 102 (FIG. 14). This can be advantageous to better contain a collapsible snare wire 142 of the snare 106, for example by physically impeding the collapsible snare wire 142 in an expanded state 144 from passing distally through the distal opening 118 of the cap 102. Thus, in some embodiments, the distal end 116 of the cap 102 comprises a lip 140 within the cavity 120 of the cap 102 for retaining the collapsible snare wire 142 within the cavity 120 of the cap 102.

The snare sheath 104 comprises a proximal end 146, a distal end 126, and a snare sheath body 148 therebetween (FIG. 1, 5-6, 11-13). The distal end 126 of the snare sheath 104 is affixed to the cap body 110 along the inner perimeter 122 of the cap body 110. The snare sheath 104 can be affixed to the cap body 110 for example by passing the snare sheath 104 through a snare-sheath hole 150 of the cap 102 from the distal end 116 of the cap 102 to the cavity 120 of the cap 102 and then affixing the snare sheath 104 to the cap body 110 along the inner perimeter 122 of the cap body 110.

The snare sheath 104 can be made from polyethylene tubing or similar tubing. The snare sheath 104 can be made with minimal internal and external diameters to accommodate a snare actuation cable 152 and the collapsible snare wire 142 of the snare 106, but with adequate wall thickness to support tissue resection.

The snare 106 comprises a snare actuation cable 152 and a collapsible snare wire 142 (FIGS. 1, 5-13).

The snare actuation cable 152 comprises a proximal end 154, a distal end 156, and a snare actuation cable body 158 therebetween (FIGS. 1, 11). The snare actuation cable 152 is disposed within the snare sheath 104. The snare actuation cable 152 is configured to be translated proximally and distally within the snare sheath 104.

The snare actuation cable 152 can be made from braided stainless steel or other similar commonly used wire materials.

The collapsible snare wire 142 comprises a base 160, an apex 162 opposite the base 160, and two opposing wire portions 164 extending therebetween (FIGS. 5-13). The collapsible snare wire 142 is disposed within the cavity 120 of the cap 102. The collapsible snare wire 142 is reversibly collapsible from an expanded state 144 to a collapsed state 166. In the expanded state 144, the two opposing wire portions 164 of the collapsible snare wire 142 have an open shape. This allows endoscopic visualization of tissue between the two opposing wire portions 164 of the collapsible snare wire 142 in the expanded state 144, i.e., visualization through the open shape formed by the two opposing wire portions 164. For example, the two opposing wire portions 164 of the collapsible snare wire 142 can have an approximately hexagonal, circular, or elliptical shape in the expanded state 144. The shape of the two opposing wire portions 164 of the collapsible snare wire 142 can be approximately hexagonal, circular, or elliptical in the expanded state 144, rather than being strictly hexagonal, circular, or elliptical, for example, based on contact between the two opposing wire portions 164 of the collapsible snare wire 142 and the inner surface 128 of the cap 102, which can result in some distortion of the shape, and/or due to flexibility of the two opposing wire portions 164 of the collapsible snare wire 142, which also can result in some distortion of the shape. The shape also can be preformed. The two opposing wire portions 164 of the collapsible snare wire 142 also can have other shapes, e.g., other polygonal shapes approximating a circular or elliptical shape. Thus, in some embodiments, the two opposing wire portions 164 of the collapsible snare wire 142 have an approximately hexagonal, circular, or elliptical shape in the expanded state 144. Also in some examples, the two opposing wire portions 164 of the collapsible snare wire 142 have a shape that is preformed.

Figure 5:
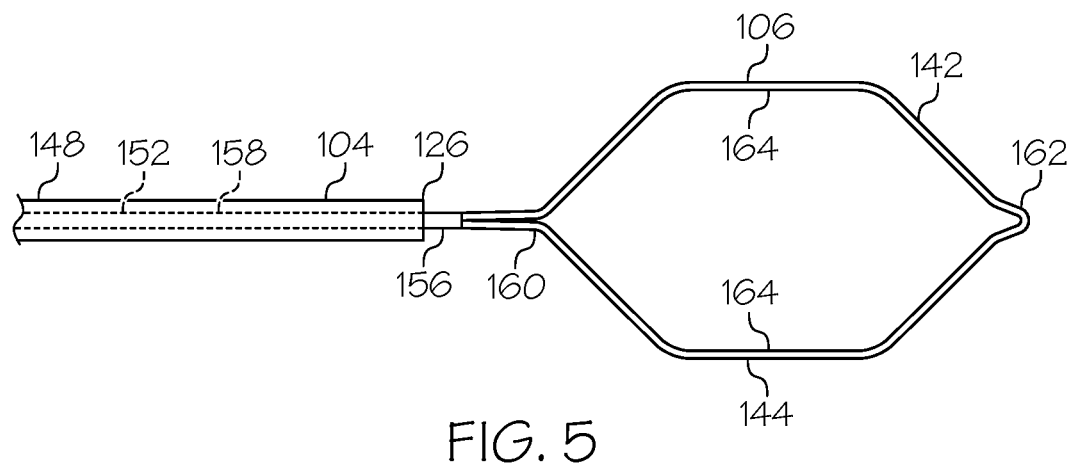
FIG. 5 is a top view of distal portions of the snare sheath and snare of the endoscopic tissue resection device of FIG. 1 in which the collapsible snare wire is fully advanced from the snare sheath and is in the expanded state.

The base 160 of the collapsible snare wire 142 is attached to the snare actuation cable 152 at or near the distal end 156 of the snare actuation cable 152 (FIG. 5).

The collapsible snare wire 142 is configured to be retracted from the cavity 120 of the cap 102 into the snare sheath 104 by translating the snare actuation cable 152 proximally within the snare sheath 104 (FIGS. 8-13). The collapsible snare wire 142 reversibly collapses from the expanded state 144 to the collapsed state 166 upon retraction. The collapsible snare wire 142 also is configured to be advanced from the snare sheath 104 into the cavity 120 of the cap 102 by translating the snare actuation cable 152 distally within the snare sheath 104. The collapsible snare wire 142 reversibly expands to the expanded state 144 upon advancement.

The collapsible snare wire 142 can be made from a material that allows the collapsible snare wire 142 to collapse into the snare sheath 104 when retracted, and to expand upon advancement from the snare sheath 104, retaining its previous shape, e.g., an approximately hexagonal, circular, or elliptical shape, repeatedly. The collapsible snare wire 142 can be made, for example, from braided stainless steel, nitinol, or other similar commonly used wire materials.

The spring wire 108 is disposed within the cavity 120 of the cap 102 and comprises a proximal end 168, a distal end 170, and a flexible portion 172 therebetween (FIGS. 7-13, 20). The spring wire 108 can be, for example, a spring wire 108 (FIG. 7) that is essentially straight in its resting state in which the proximal end 168 and the distal end 170 are opposite ends of the spring wire 108. The spring wire 108 also can be, for example, a spring wire 108 (FIG. 20) that has been folded at or near its middle, such that the two ends of the spring wire 108 become the proximal end 168 of the spring wire 108 and the site of the fold becomes the distal end 170 of the spring wire 108.

Figure 8:
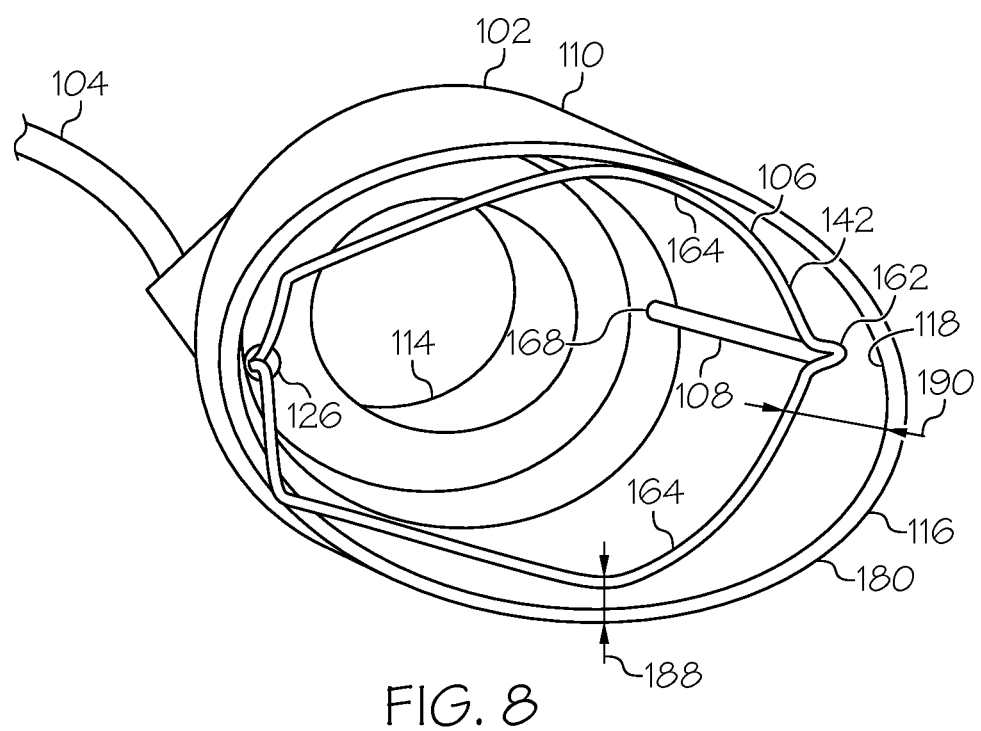
FIG. 8 is a perspective front view of the cap, distal portions of the snare sheath and snare, and the spring wire of the endoscopic tissue resection device of FIG. 1 in which the collapsible snare wire is fully advanced from the snare sheath, the collapsible snare wire is in the expanded state, and the spring wire is in the resting state. Based on the orientation and stabilization provided by the spring wire and the two opposing wire portions of the collapsible snare wire being positioned in apposition to the distal opening of the cap, the collapsible snare wire aligns closely to the inner circumference of the distal opening of the cap and flush to the distal edge of the distal end of the cap. The fully open collapsible snare wire is seen aligning with the perimeter of the distal cap edge. The spring wire is seen aligned longitudinally with the cap wall.
Figure 9:
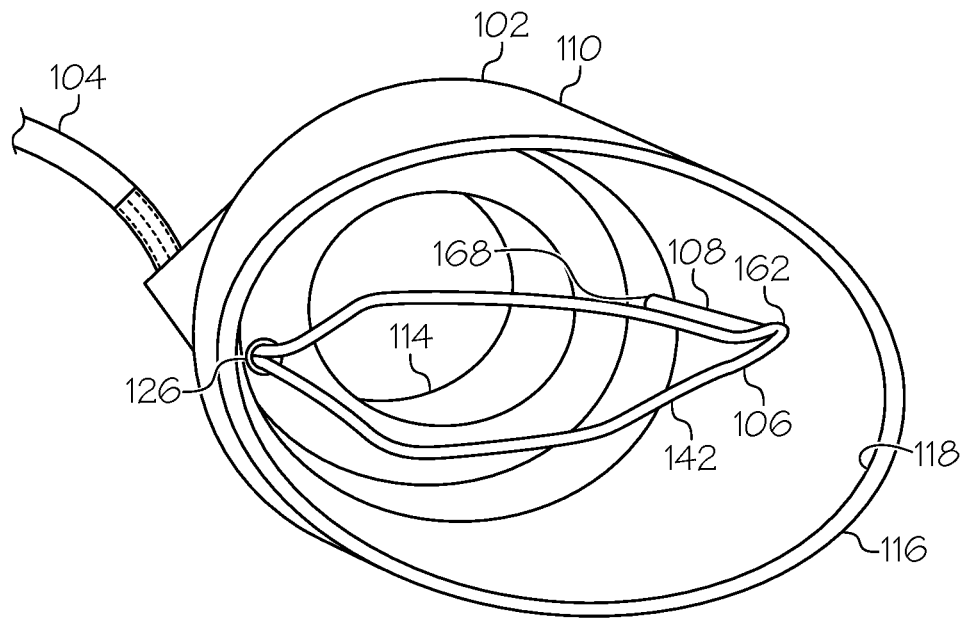
FIG. 9 is a perspective front view of the cap, distal portions of the snare sheath and snare, and the spring wire of the endoscopic tissue resection device of FIG. 1 in which the collapsible snare wire is partially retracted into the snare sheath, the collapsible snare wire is collapsing from the expanded state to the collapsed state, and the spring wire is deflecting from the resting state to the deflected state. The partially closed collapsible snare wire is seen narrowing away from the distal edge of the distal end of the cap. The spring wire is beginning to flex away from the cap wall.

The proximal end 168 of the spring wire 108 is attached to the cap body 110 at or near the proximal end 112 of the cap 102 (FIG. 8, 11). The proximal end 168 of the spring wire 108 can be attached to the cap body 110 for example by adhering the spring wire 108 to the cap body 110 within a spring-wire hole 174 within the cap body 110.

The distal end 170 of the spring wire 108 is attached to the apex 162 of the collapsible snare wire 142 (FIGS. 11-13, 19, 21). This can be accomplished for example by welding, bonding, use of a collar, sheath, tube, or other similar structure, or crimping, among other approaches. For example, for a spring wire 108 that is essentially straight in its resting state, the distal end 170 of the spring wire 108 can be attached to the apex 162 of the collapsible snare wire 142 by welding to form a weld site 204. Also for example, for a spring wire 108 that has been folded at or near its middle, the distal end 170 of the spring wire 108, i.e. the site of the fold of the spring wire 108, can be attached to the apex 162 of the collapsible snare wire 142 by placing the folded spring wire 108 over the snare apex 162 and securing the junction with a collar 206 pushed tightly against the apex 162. A sheath, tube, or other similar structure can also be used instead of, or in addition to, the collar 206. The collar 206, or sheath, tube, or similar structure, can be made from a material, such as a plastic, that provides insulation during use of standard electrical surgical energy.

The spring wire 108 is reversibly deflectable from a resting state 176 to a deflected state 178. The spring wire 108 is in the resting state 176 when the collapsible snare wire 142 is disposed within the cavity 120 of the cap 110. The spring wire 108 deflects to the deflected state 178 when the collapsible snare wire 142 is retracted into the snare sheath 104.

In the resting state 176 the spring wire 108 orients and stabilizes the apex 162 of the collapsible snare wire 142 within the cap 102, at or near the distal opening 114 of the cap 102, opposite the distal end 126 of the snare sheath 104, such that the two opposing wire portions 164 of the collapsible snare wire 142 are positioned in apposition to the distal opening 118 of the cap 102 (FIGS. 8, 11). As noted above, in the expanded state 144, the two opposing wire portions 164 of the collapsible snare wire 142 have an open shape, allowing endoscopic visualization of tissue between the two opposing wire portions 164 of the collapsible snare wire 142 in the expanded state 144. By orienting and stabilizing the apex 162 of the collapsible snare wire 142 this way, the spring wire 108 contributes in positioning the collapsible snare wire 142 to allow endoscopic visualization of tissue beyond the distal opening 118 of the cap 102.

During deflection the spring wire 108 bends along an arced path 124 to the snare sheath 104 (FIGS. 9, 10, 12, 13). The distal end 126 of the snare sheath 104 is recessed into the cavity 120 of the cap 102 relative to the distal end 170 of the spring wire 108 to allow the spring wire 108 to bend along the arced path 124.

The spring wire 108 can be made of a spring material, such as nitinol, e.g., 0.025 inch (0.635 mm) diameter nitinol, or plastic.

The proximal end 168 of the spring wire 108 can be attached directly to the cap 102, opposite, e.g., approximately 180 degrees, from the distal end 126 of the snare sheath 104, near the site of fixation of the cap 102 to the endoscope. The spring wire 108 can be disposed within the cavity 120 of the cap 102 in close proximity to the inner surface 128 of the cap 102. The spring wire 108 can be oriented generally parallel to the longitudinal axis of the endoscope and the portion of the snare sheath 104 oriented along the endoscope. The distal end 170 of the spring wire 108 is located near the distal edge 180 of the distal end 116 of the cap 102. The distal end 170 of the spring wire 108 is attached to the apex 162 of the snare 106 in a manner so as avoid or minimize interfering with collapse of the collapsible snare wire 142, and thus to avoid or minimize interfering with closure of the two opposing wire portions 164 of the collapsible snare wire 142. The length of the spring wire 108 can be made proportionate to the depth, diameter, and contour of the cap 102 to provide for the arced path 124 of the spring wire 108 from the distal edge 180 of the distal end 116 of the cap 102 to the snare sheath 104.

The spring wire 108 has sufficient "spring" properties to serve the features below, while not restricting closing and reopening of the collapsible snare wire 142.

The spring wire 108 contributes at least three distinct functions to the device 100. First, the spring wire 108 stabilizes the apex 162 of the collapsible snare wire 142 at the distal end 116 of the cap 102, ensuring that tissue retracted into the cap 102 does not also retract the collapsible snare wire 142 into the cap 102. Second, the spring wire 108 ensures that the two opposing wire portions 164 of the collapsible snare wire 142 open to a position to appose the inner circumference of the distal opening 118 of the cap 102. Third, the spring wire 108 stabilizes the collapsible snare wire 142 against the tissue to be resected, reducing the ability for the tissue to slip through the collapsible snare wire 142.

The endoscopic tissue resection device 100 can be operated to accomplish resection of a tissue as follows (FIGS. 1, 8, 11, 14-16).

The cap 102 of the endoscopic tissue resection device 100 is attached to the distal end of an endoscope at the proximal end 112 of the cap 102 (FIGS. 8, 11). The attachment can be accomplished, for example, by use of a compression fitting, such as a compression band or similar mechanism, or other similar low profile attachment. The cavity 120 of the cap 102 is maintained in fluid communication with a source of suction, for example through an internal endoscope channel of the endoscope, by way of the proximal opening 114 of the cap 102.

A snare actuator handle 182 is attached to the snare actuation cable 152 (FIG. 1). The snare sheath 104 terminates at its proximal end 146 at the snare actuator handle 182. The snare actuator handle 182 thus allows control of retraction and advancement of the collapsible snare wire 142 via the snare actuation cable 152, facilitating manual opening and closing of the two opposing wire portions 164 of the collapsible snare wire 142 for resection of tissue.

During operation of the endoscopic tissue resection device 100, the snare sheath 104 is external to the endoscope over the entire length of endoscope.

The collapsible snare wire 142 is positioned within the cavity 120 of the cap 102 such that the collapsible snare wire 142 is in the expanded state 144 and the spring wire 108 is in the resting state 166 (FIGS. 8, 11). As noted above, in the resting state 166 the spring wire 108 orients and stabilizes the apex 162 of the collapsible snare wire 142 within the cap 102, at or near the distal opening 118 of the cap 102, opposite the distal end 126 of the snare sheath 104, such that the two opposing wire portions 164 of the collapsible snare wire 142 are positioned in apposition to the distal opening 118 of the cap 102. Also as noted, the two opposing wire portions 164 of the collapsible snare wire 142 can have a preformed, approximately hexagonal, circular, or elliptical shape.

Based on the orientation and stabilization provided by the spring wire 108 and the two opposing wire portions 164 of the collapsible snare wire 142 being positioned in apposition to the distal opening 118 of the cap 102, the collapsible snare wire 142 aligns closely to the inner circumference of the distal opening 118 of the cap 102 and flush to the distal edge 180 of the distal end 116 of the cap 102.

Tissue 200 is retracted into the cap 102 by suction (FIG. 14). The alignment of the collapsible snare wire 142 close to the inner circumference of the distal opening 118 of the cap 102 and flush to the distal opening 118 of the cap 102 ensures that upon retraction of tissue 200 into the cap 102 by suction the tissue 200 becomes encircled and entrapped by the collapsible snare wire 142.

Figure 15:
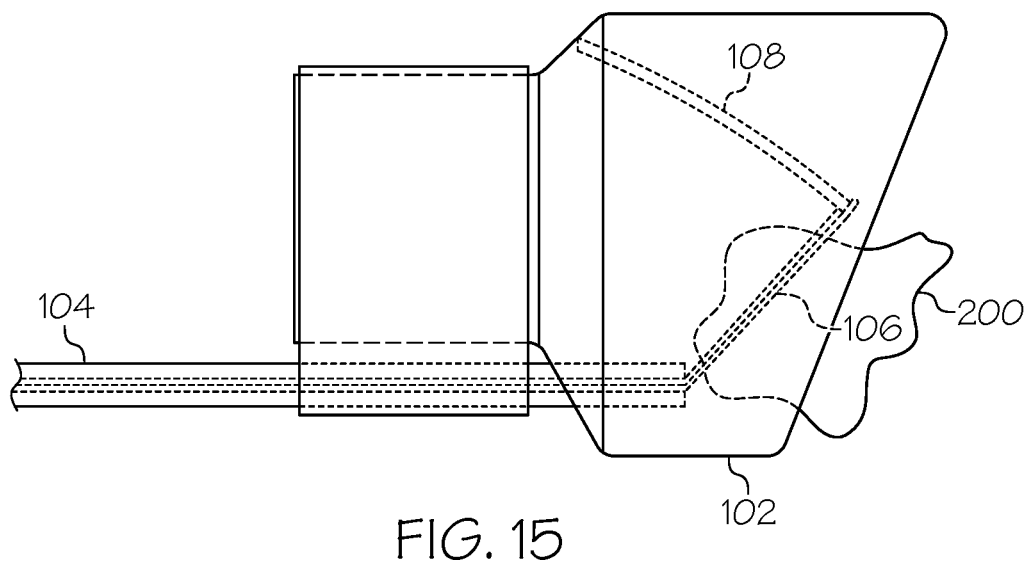
FIG. 15 is a side view of the cap, distal portions of the snare sheath and snare, and the spring wire as shown in FIG. 9, in which tissue has been retracted into the cap and is being resected by the collapsible snare wire of the snare.

The snare actuation cable 152 is then translated proximally within the snare sheath 104 to retract the collapsible snare wire 142 into the snare sheath 104 (FIG. 15). This can be accomplished, for example, by use of the snare actuator handle 182 attached to the snare actuation cable 152.

Figure 16:
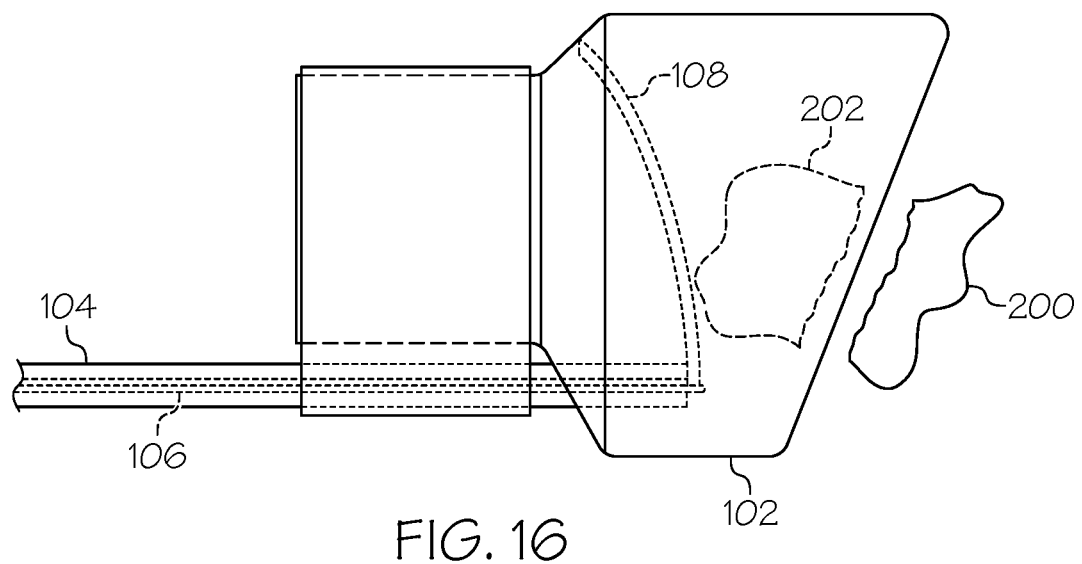
FIG. 16 is a side view of the cap, distal portions of the snare sheath and snare, and the spring wire as shown in FIG. 10, in which tissue has been retracted into the cap and has been resected by the collapsible snare wire of the snare.
Figure 17:
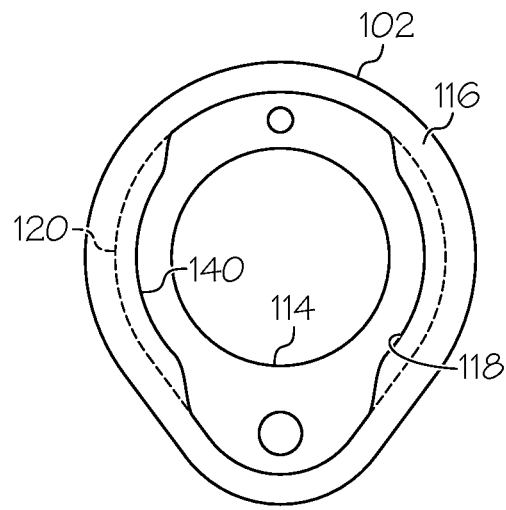
FIG. 17 is a side view of the cap of the endoscopic tissue resection device of FIG. 1 including a lip.

Upon retraction of the collapsible snare wire 142 into the snare sheath 104, the collapsible snare wire 142 collapses to the collapsed state 166 (FIG. 16). As the collapsible snare wire 142 collapses, the tissue 200 entrapped by the collapsible snare wire 142 is resected.

Also upon retraction of the collapsible snare wire 142 into the snare sheath 104, the spring wire 108 bends along its arced path 124 to the snare sheath 104, remaining attached to the apex 162 of the collapsible snare wire 142.

Figure 10:
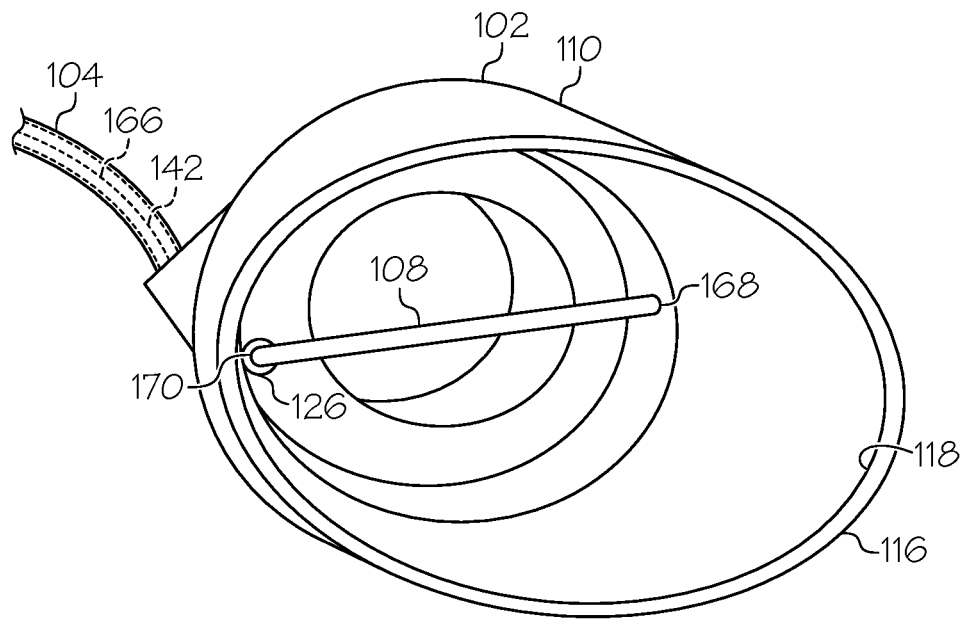
FIG. 10 is a perspective front view of the cap, distal portions of the snare sheath and snare, and the spring wire of the endoscopic tissue resection device of FIG. 1 in which the collapsible snare wire is fully retracted into the snare sheath, the collapsible snare wire is in the collapsed state, and the spring wire is in the deflected state. The completely closed collapsible snare wire is retracted into the snare sheath. The spring wire is flexed across the diameter of the cap.

Following resection of the tissue 200, the collapsible snare wire 142 can be advanced to the cavity 120 of the cap 102 again by translating the snare actuation cable 152 distally within the snare sheath 104 (FIGS. 10, 13). This can be done by use of the snare actuator handle 182 attached to the snare actuation cable 152. Upon advancement, the collapsible snare wire 142 expands to its expanded state 144, e.g., returning to its preformed, approximately hexagonal, circular, or elliptical shape. The spring wire 108, still attached to the apex 162 of the collapsible snare wire 108, returns to its resting state 166, and again orients and stabilizes the apex 162 of the collapsible snare wire 142 within the cap 102, at or near the distal opening 118 of the cap 102, opposite the distal end 126 of the snare sheath 104, such that the two opposing wire portions 164 of the collapsible snare wire 142 are positioned in apposition to the distal opening 118 of the cap 102. Based on the orientation and stabilization provided by the spring wire 108 and the two opposing wire portions 164 of the collapsible snare wire 142 being positioned in apposition to the distal opening 118 of the cap 102, the collapsible snare wire 142 again aligns closely to the inner circumference of the distal opening 118 of the cap 102 and flush to the distal edge 180 of the distal end 116 of the cap 102.

Also following resection of the tissue 200, the resected tissue 202 can be retrieved.

During operation, the entirety of the endoscopic tissue resection device 100 is disposed externally to the endoscope, advantageously freeing the internal endoscope channel for use with an additional instrument device. The absence of a device in the internal endoscope channel also advantageously increases available suction provided by the endoscope, enabling greater tissue retraction.

Considering the endoscopic tissue resection device 100 further, as noted above, based on the orientation and stabilization provided by the spring wire 108 and the two opposing wire portions 164 of the collapsible snare wire 142 being positioned in apposition to the distal opening 118 of the cap 102, the collapsible snare wire 142 aligns closely to the inner circumference of the distal opening 118 of the cap 102 and flush to the distal edge 180 of the distal end 116 of the cap 102 (FIGS. 8, 11). Also as noted, the alignment of the collapsible snare wire 142 close to the inner circumference of the distal opening 118 of the cap 102 and flush to the distal opening 118 of the cap 102 ensures that upon retraction of tissue into the cap 102 by suction the tissue becomes encircled and entrapped by the collapsible snare wire 142.

Thus, in some embodiments, the distal opening 118 of the cap 102 has an inner circumference 184 having a diameter 186, and the collapsible snare wire 142 in the expanded state 144 apposes the inner circumference 184 of the distal opening 118 of the cap 102 closely enough that any gaps 188 between the two opposing wire portions 164 of the collapsible snare wire 142 and the inner circumference 184 of the distal opening 118 of the cap 102 are not more than 10%, 8%, 6%, 4%, or 2% of the diameter 186 of the inner circumference 184 of the distal opening 118 of the cap 102 (FIGS. 2, 3, 8).

In some embodiments, the distal opening 118 of the cap 102 has an inner circumference 184, and the collapsible snare wire 142 in the expanded state 144 apposes the inner circumference 184 of the distal opening 118 of the cap 102 closely enough that any gaps 190 between the two opposing wire portions 164 of the collapsible snare wire 142 and the inner circumference 184 of the distal opening 118 of the cap 102 are not more than 5 mm, 4 mm, 3 mm, 2 mm, or 1 mm (FIGS. 2, 3, 8).

In some embodiments, the distal end 116 of the cap 102 has a distal edge 180, the cavity 120 of the cap 102 has an inner depth 132, and the collapsible snare wire 142 in the expanded state 144 rests sufficiently flush to the distal edge 180 of the distal end 116 of the cap 102 that any gaps 190 between the two opposing wire portions 164 of the collapsible snare wire 142 and the distal edge 180 of the distal end 118 of the cap 102 are not more than 20%, 16%, 12%, 8%, or 4% of the inner depth 132 of the cavity 120 of the cap 102 (FIGS. 2, 3, 8).

In some embodiments, the distal end 116 of the cap 102 has a distal edge 180, the cap 102 has an axis 194 extending from the proximal end 112 of the cap 102 to the distal end 116 of the cap 102, and the collapsible snare wire 142 in the expanded state 144 rests sufficiently flush to the distal edge 180 of the distal end 116 of the cap 102 that any gaps 190 between the two opposing wire portions 164 of the collapsible snare wire 142 and the distal edge 180 of the distal end 116 of the cap 102 are not more than 5 mm, 4 mm, 3 mm, 2 mm, or 1 mm as measured along the axis 194 (FIGS. 2, 3, 8).

Figure 6:
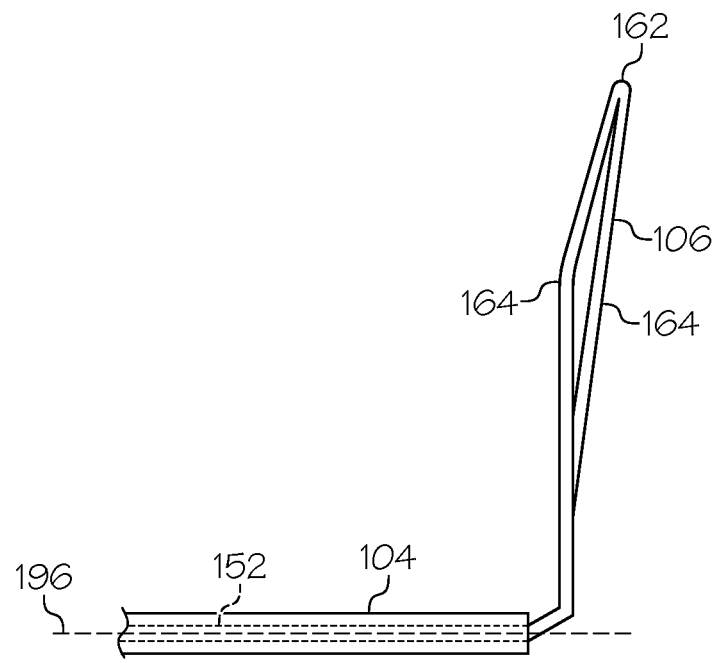
FIG. 6 is a side view of distal portions of the snare sheath and snare of the endoscopic tissue resection device of FIG. 1 in which the collapsible snare wire is partially retracted into the snare sheath.
Figure 7:
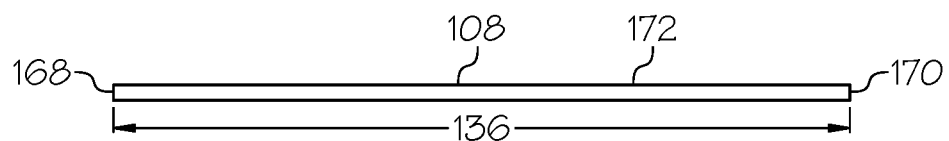
FIG. 7 is a side view of the spring wire of the endoscopic tissue resection device of FIG. 1 in which the spring wire is straight in its resting state.

The collapsible snare wire 142 can be further shaped such that it exits the snare sheath 104 angled relative to a longitudinal orientation of the snare sheath 104 along an endoscope (FIGS. 6, 11). This contributes to allowing the size and shape of the collapsible snare wire 142 in the expanded state 144 to closely appose the inner circumference of the distal opening 118 of the cap 102 and rest essentially flush to a distal edge 180 of the distal end 116 of the cap 102. Thus, in some embodiments the snare sheath 104 has an axis 196 extending from its proximal end 146 to its distal end 126, and the collapsible snare wire 142 is shaped to deflect from the axis 196 during advancement of the collapsible snare wire 142 from the distal end 126 of the snare sheath 104.

Figure 18:
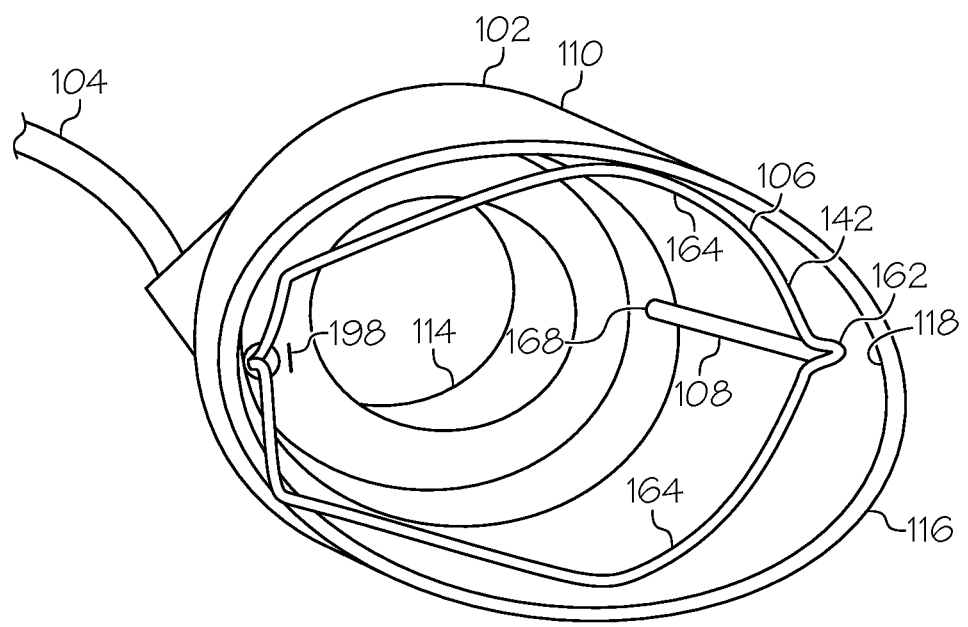
FIG. 18 is a perspective front view of the cap, distal portions of the snare sheath and snare, and the spring wire of the endoscopic tissue resection device of FIG. 1 in which a blade is disposed in the cavity of the cap adjacent the distal end of the snare sheath.
Figure 19:
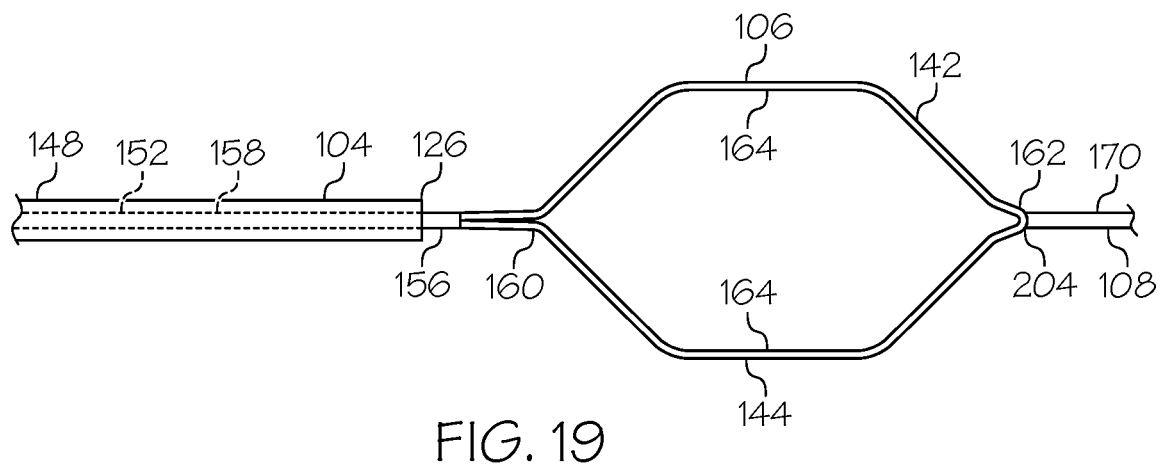
FIG. 19 is a top view of distal portions of the snare sheath and snare and a distal portion of the spring wire of the endoscopic tissue resection device of FIG. 1 in which the collapsible snare wire is fully advanced from the snare sheath and is in the expanded state, and the distal end of the spring wire is attached to the apex of the snare at a weld site.
Figure 20:
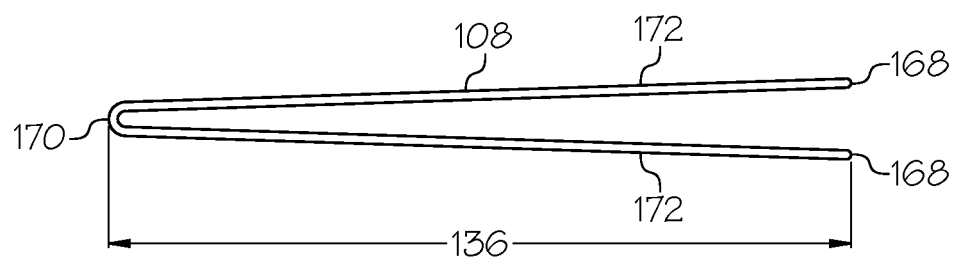
FIG. 20 is a side view of another embodiment of the spring wire of the endoscopic tissue resection device of FIG. 1 in which the spring wire has been folded upon itself.
Figure 21:
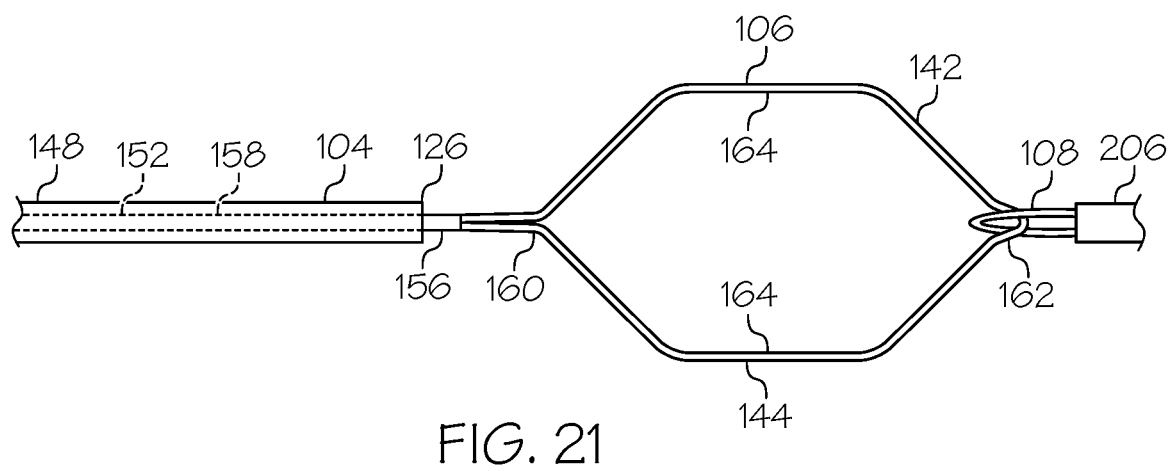
FIG. 21 is a top view of distal portions of the snare sheath and snare and a distal portion of the spring wire of the endoscopic tissue resection device of FIG. 1, in which the spring wire has been folded upon itself, the collapsible snare wire is fully advanced from the snare sheath and is in the expanded state, and the distal end of the spring wire is attached to the apex of the snare by placing the folded spring wire over the apex of the snare and securing the junction with a collar.

A blade 198 can be disposed near where the distal end 126 of the snare sheath 104 is affixed along the inner perimeter 122 of the cap body 110 such that tissues entrapped by the collapsible snare wire 142 can be better sheared as the collapsible snare wire 142 collapses (FIG. 18). Thus, in some embodiments the endoscopic tissue resection device 100 further comprises a blade 198 disposed in the cavity 120 of the cap 102 adjacent the distal end 126 of the snare sheath 104. According to these embodiments, the blade 198 can be oriented to shear tissue entrapped by the collapsible snare wire 142 as the collapsible snare wire 142 collapses, e.g. the blade 198 can be oriented distally.

A snare actuator handle 182 used with the endoscopic tissue resection device 100 can include an attachment for standard electrical surgical energy. In some embodiments, the collapsible snare wire 142 diameter may also vary, allowing for "cold" (no energy) or "hot" (electrical energy) applications for cutting a tissue and/or use of the snare 106 for grasping a tissue. In the case of a "hot" snare 106, the spring wire 108 should be insulated, e.g., with a plastic collar, to reduce energy spread to the tissue through the spring wire 108.

In some embodiments the endoscopic tissue resection device 100 can include additional spring wires 108, for example up to a total of two, three, four, or five spring wires 108, to position the two opposing wire portions 164 of the collapsible snare wire 142 in apposition to the distal opening 118 of the cap 102, e.g., to restore an approximately hexagonal, circular, or elliptical shape of the two opposing wire portions 164 of the collapsible snare wire 142, so that the collapsible snare wire 142 aligns closely to the inner circumference of the distal opening 118 of the cap 102 and flush to the distal edge 180 of the distal end 116 of the cap 102. In accordance with these embodiments, these proximal ends 168 of the additional spring wires 108 are attached at or near the proximal end 112 of the cap 102, and the distal ends 170 are attached to the collapsible snare wire 142 at points of fixation ranging from 90° to 270°, relative to the base 160 of the collapsible snare wire 142 corresponding to 0° and the apex 162 of the collapsible snare wire 142 corresponding to 180°. Attaching the additional spring wires 108 at points of fixation this way can provide improved alignment and positioning of the two opposing wire portions 164 of the collapsible snare wire 142 relative to the inner circumference of the distal opening 118 of the cap 102 and the distal edge 180 of the distal end 116 of the cap 102 without interfering with expansion of the collapsible snare wire 142.

Also in some embodiments the endoscopic tissue resection device 100 can include mechanisms in addition to the one or more spring wires 108 to accomplish this, for example an elastic membrane.

In some embodiments, the apex of the collapsible snare wire may be fixed and the collapsible snare wire or sheath may be the spring component, such that the sheath moves toward the apex upon retraction of the snare wire.

In some embodiments, the apex of the collapsible snare wire and the snare sheath may both contain spring components such that each moves toward each other, closing in or near the center of the cap.

In some embodiments the endoscopic tissue resection device 100 can be used for tissue evaluation.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

Clauses

1. An endoscopic tissue resection device configured to be attached at a distal tip of an endoscope, the device comprising a cap, a snare sheath, a snare, and a spring wire, wherein:
   the cap comprises a cap body, a proximal end, a proximal opening, a distal end, and a distal opening;
   the cap body defines a cavity for retraction of a tissue and has an inner perimeter;
   the snare sheath comprises a proximal end, a distal end, and a snare sheath body therebetween;
   the distal end of the snare sheath is affixed to the cap body along the inner perimeter of the cap body;
   the snare comprises a snare actuation cable and a collapsible snare wire;
   the snare actuation cable comprises a proximal end, a distal end and a snare actuation cable body therebetween, is disposed within the snare sheath, and is configured to be translated proximally and distally within the snare sheath;
   the collapsible snare wire comprises a base, an apex opposite the base, and two opposing wire portions extending therebetween, is disposed within the cavity of the cap, and is reversibly collapsible from an expanded state to a collapsed state;

the base of the collapsible snare wire is attached to the snare actuation cable at or near the distal end of the snare actuation cable;

the collapsible snare wire is configured to be retracted from the cavity of the cap into the snare sheath by translating the snare actuation cable proximally within the snare sheath, the collapsible snare wire reversibly collapsing from the expanded state to the collapsed state upon retraction, and to be advanced from the snare sheath into the cavity of the cap by translating the snare actuation cable distally within the snare sheath, the collapsible snare wire reversibly expanding to the expanded state upon advancement;

the spring wire is disposed within the cavity of the cap and comprises a proximal end, a distal end, and a flexible portion therebetween;

the proximal end of the spring wire is attached to the cap body at or near the proximal end of the cap;

the distal end of the spring wire is attached to the apex of the collapsible snare wire;

the spring wire is reversibly deflectable from a resting state to a deflected state, the spring wire being in the resting state when the collapsible snare wire is disposed within the cavity of the cap and deflecting to the deflected state when the collapsible snare wire is retracted into the snare sheath;

in the resting state the spring wire orients and stabilizes the apex of the collapsible snare wire within the cap, at or near the distal opening of the cap, opposite the distal end of the snare sheath, such that the two opposing wire portions of the collapsible snare wire are positioned in apposition to the distal opening of the cap;

during deflection the spring wire bends along an arced path to the snare sheath; and the distal end of the snare sheath is recessed into the cavity of the cap relative to the distal end of the spring wire to allow the spring wire to bend along the arced path.

2. The endoscopic tissue resection device according to clause 1, wherein the cap has an outer diameter of 0.5 to 1.5 cm.

3. The endoscopic tissue resection device according to clause 1 or 2, wherein the cavity of the cap has an inner depth of 0.5 cm to 1.5 cm.

4. The endoscopic tissue resection device according to any one of clauses 1-3, wherein the cavity of the cap has an inner diameter, the spring wire has a length, and the inner diameter of the cavity of the cap is greater than the length of the spring wire.

5. The endoscopic tissue resection device according to any one of clauses 1-4, wherein the distal end of the cap has an oblique profile.

6. The endoscopic tissue resection device according to any one of clauses 1-5, wherein the distal end of the cap comprises a lip within the cavity of the cap for retaining the collapsible snare wire within the cavity of the cap.

7. The endoscopic tissue resection device according to any one of clauses 1-6, wherein the two opposing wire portions of the collapsible snare wire have an approximately hexagonal, circular, or elliptical shape in the expanded state.

8. The endoscopic tissue resection device according to any one of clauses 1-7, wherein the distal opening of the cap has an inner circumference having a diameter, and the collapsible snare wire in the expanded state apposes the inner circumference of the distal opening of the cap closely enough that any gaps between the two opposing wire portions of the collapsible snare wire and the inner circumference of the distal opening of the cap are not more than 10%, 8%, 6%, 4%, or 2% of the diameter of the inner circumference of the distal opening of the cap.

9. The endoscopic tissue resection device according to any one of clauses 1-8, wherein the distal opening of the cap has an inner circumference, and the collapsible snare wire in the expanded state apposes the inner circumference of the distal opening of the cap closely enough that any gaps between the two opposing wire portions of the collapsible snare wire and the inner circumference of the distal opening of the cap are not more than 5 mm, 4 mm, 3 mm, 2 mm, or 1 mm.

10. The endoscopic tissue resection device according to any one of clauses 1-9, wherein the distal end of the cap has a distal edge, the cavity of the cap has an inner depth, and the collapsible snare wire in the expanded state rests sufficiently flush to the distal edge of the distal end of the cap that any gaps between the two opposing wire portions of the collapsible snare wire and the distal edge of the distal end of the cap are not more than 20%, 16%, 12%, 8%, or 4% of the inner depth of the cavity of the cap.

11. The endoscopic tissue resection device according to any one of clauses 1-10, wherein the distal end of the cap has a distal edge, the cap has an axis extending from the proximal end of the cap to the distal end of the cap, and the collapsible snare wire in the expanded state rests sufficiently flush to the distal edge of the distal end of the cap that any gaps between the two opposing wire portions of the collapsible snare wire and the distal edge of the distal end of the cap are not more than 5 mm, 4 mm, 3 mm, 2 mm, or 1 mm as measured along the axis.

12. The endoscopic tissue resection device according to any one of clauses 1-11, wherein the snare sheath has an axis extending from its proximal end to its distal end, and the collapsible snare wire is shaped to deflect from the axis during advancement of the collapsible snare wire from the distal end of the snare sheath.

13. The endoscopic tissue resection device according to any one of clauses 1-12, wherein the device further comprises a blade disposed in the cavity of the cap adjacent the distal end of the snare sheath.

The invention claimed is:

1. An endoscopic tissue resection device configured to be attached at a distal tip of an endoscope, the device comprising a cap, a snare sheath, a snare, and a spring wire, wherein:

the cap comprises a cap body, a proximal end, a proximal opening, a distal end, and a distal opening;

the cap body defines a cavity for retraction of a tissue and has an inner perimeter;

the snare sheath comprises a proximal end, a distal end, and a snare sheath body therebetween;

the distal end of the snare sheath is affixed to the cap body along the inner perimeter of the cap body;

the snare comprises a snare actuation cable and a collapsible snare wire;

the snare actuation cable comprises a proximal end, a distal end and a snare actuation cable body therebetween, is disposed within the snare sheath, and is configured to be translated proximally and distally within the snare sheath;

the collapsible snare wire comprises a base, an apex opposite the base, and two opposing wire portions extending therebetween, is disposed within the cavity of the cap, and is reversibly collapsible from an expanded state to a collapsed state;

the base of the collapsible snare wire is attached to the snare actuation cable at or near the distal end of the snare actuation cable;

the collapsible snare wire is configured to be retracted from the cavity of the cap into the snare sheath by translating the snare actuation cable proximally within the snare sheath, the collapsible snare wire reversibly collapsing from the expanded state to the collapsed state upon retraction, and to be advanced from the snare sheath into the cavity of the cap by translating the snare actuation cable distally within the snare sheath, the collapsible snare wire reversibly expanding to the expanded state upon advancement;

the spring wire is disposed within the cavity of the cap and comprises a proximal end, a distal end, and a flexible portion therebetween;

the proximal end of the spring wire is attached to the cap body at or near the proximal end of the cap;

the distal end of the spring wire is attached to the apex of the collapsible snare wire;

the spring wire is reversibly deflectable from a resting state to a deflected state, the spring wire being in the resting state when the collapsible snare wire is disposed within the cavity of the cap and deflecting to the deflected state when the collapsible snare wire is retracted into the snare sheath;

in the resting state the spring wire orients and stabilizes the apex of the collapsible snare wire within the cap, at or near the distal opening of the cap, opposite the distal end of the snare sheath, such that the two opposing wire portions of the collapsible snare wire are positioned in apposition to the distal opening of the cap;

during deflection the spring wire bends along an arced path to the snare sheath; and the distal end of the snare sheath is recessed into the cavity of the cap relative to the distal end of the spring wire to allow the spring wire to bend along the arced path.

2. The endoscopic tissue resection device according to claim 1, wherein the cap has an outer diameter of 0.5 to 1.5 cm.

3. The endoscopic tissue resection device according to claim 1, wherein the cavity of the cap has an inner depth of 0.5 cm to 1.5 cm.

4. The endoscopic tissue resection device according to claim 1, wherein the cavity of the cap has an inner diameter, the spring wire has a length, and the inner diameter of the cavity of the cap is greater than the length of the spring wire.

5. The endoscopic tissue resection device according to claim 1, wherein the distal end of the cap has an oblique profile.

6. The endoscopic tissue resection device according to claim 1, wherein the distal end of the cap comprises a lip within the cavity of the cap for retaining the collapsible snare wire within the cavity of the cap.

7. The endoscopic tissue resection device according to claim 1, wherein the two opposing wire portions of the collapsible snare wire have an approximately hexagonal, circular, or elliptical shape in the expanded state.

8. The endoscopic tissue resection device according to claim 1, wherein the distal opening of the cap has an inner circumference having a diameter, and the collapsible snare wire in the expanded state apposes the inner circumference of the distal opening of the cap closely enough that any gaps between the two opposing wire portions of the collapsible snare wire and the inner circumference of the distal opening of the cap are not more than 10%, 8%, 6%, 4%, or 2% of the diameter of the inner circumference of the distal opening of the cap.

9. The endoscopic tissue resection device according to claim 1, wherein the distal opening of the cap has an inner circumference, and the collapsible snare wire in the expanded state apposes the inner circumference of the distal opening of the cap closely enough that any gaps between the two opposing wire portions of the collapsible snare wire and the inner circumference of the distal opening of the cap are not more than 5 mm, 4 mm, 3 mm, 2 mm, or 1 mm.

10. The endoscopic tissue resection device according to claim 1, wherein the distal end of the cap has a distal edge, the cavity of the cap has an inner depth, and the collapsible snare wire in the expanded state rests sufficiently flush to the distal edge of the distal end of the cap that any gaps between the two opposing wire portions of the collapsible snare wire and the distal edge of the distal end of the cap are not more than 20%, 16%, 12%, 8%, or 4% of the inner depth of the cavity of the cap.

11. The endoscopic tissue resection device according to claim 1, wherein the distal end of the cap has a distal edge, the cap has an axis extending from the proximal end of the cap to the distal end of the cap, and the collapsible snare wire in the expanded state rests sufficiently flush to the distal edge of the distal end of the cap that any gaps between the two opposing wire portions of the collapsible snare wire and the distal edge of the distal end of the cap are not more than 5 mm, 4 mm, 3 mm, 2 mm, or 1 mm as measured along the axis.

12. The endoscopic tissue resection device according to claim 1, wherein the snare sheath has an axis extending from its proximal end to its distal end, and the collapsible snare wire is shaped to deflect from the axis during advancement of the collapsible snare wire from the distal end of the snare sheath.

13. The endoscopic tissue resection device according to claim 1, wherein the device further comprises a blade disposed in the cavity of the cap adjacent the distal end of the snare sheath.

* * * * *